United States Patent [19]

Dehne et al.

[11] Patent Number: 5,420,148
[45] Date of Patent: May 30, 1995

[54] FUNGICIDAL COMPOSITIONS

[75] Inventors: Heinz-Wilhelm Dehne, Monheim; Winfried Lunkenheimer, Wuppertal, both of Germany

[73] Assignee: Bayer Aktiengesellschaft, Leverkusen, Germany

[21] Appl. No.: 263,297

[22] Filed: Jun. 21, 1994

[30] Foreign Application Priority Data

Jun. 25, 1993 [DE] Germany .......... 43 21 206.9

[51] Int. Cl.$^6$ .......... A01N 41/02; A01N 43/32; A01N 43/52
[52] U.S. Cl. .......... 514/395; 514/452; 514/600
[58] Field of Search .......... 514/395, 600, 452

[56] References Cited

U.S. PATENT DOCUMENTS 5,310,747  5/1994  Enomoto et al. .......... 514/395

FOREIGN PATENT DOCUMENTS 0517476  12/1992  European Pat. Off. .

OTHER PUBLICATIONS

Worthing et al., The Pesticides Manual, 9th Ed., (1991) p. 827.

*Primary Examiner*—Allen J. Robinson
*Attorney, Agent, or Firm*—Sprung Horn Kramer & Woods

[57] ABSTRACT

A novel fungicidal composition comprising a fungicidally effective amount of a combination consisting of the known 2-cyanobenzimidazole of the formula

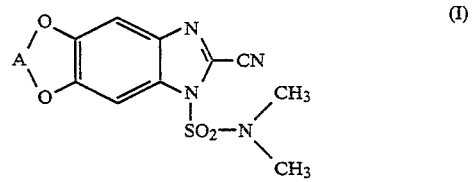

(I)

in which A has the meanings given in the description and at least one other known fungicidally active compound selected from the group mentioned in the specification.

The novel compositions show a synergistic activity.

4 Claims, No Drawings

FUNGICIDAL COMPOSITIONS

The present invention relates to new active compound combinations which consist, on the one hand, of the known 2-cyanobenzimidazoles of the formula.

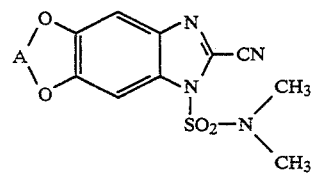

(I)

A=—CF$_2$—      (I-1)

A=—CF$_2$—CF$_2$—      (I-2)

and, on the other hand, of other known fungicidal active compounds and which are highly suitable for combating fungi.

It has already been disclosed that the 2-cyanobenzimidazoles of the formula (I) have fungicidal properties (cf. EP-OS (European Published Specification) 0 517 476). The activity of these substances is good; however, it leaves something to be desired in some cases when low application rates are used.

Furthermore, it has already been disclosed that a large number of azole derivatives., aryl benzyl ethers, benzamides, morpholin compounds and other heterocycles can be used for combating fungi (cf. K. H. Büchel "Pflanzenschutz und Schädlingsbekämpfung", [Crop Protection and Pest Control], pages 140 to 153, Georg Thieme Verlag, Stuttgart 1977, EP-OS (European Published Spefification) 0 040 345, DE-OS (German Published Specification) 2 324 010, DE-OS (German Published Specification) 2 201 063, EP-OS (European Published Specification) 0 112 284, EP-OS (European Published Specification) 0 304 758 and DD-PS (East German Patent) 140 412).

Other fungicidal active compound combinations which are known comprise the 2-cyanobenzimidazoles of the formula (I) and other known fungicidal active compounds (cf. EP-OS (European Published Specification) 0 517 476).

However, the activity of the known fungicidal active compounds in the form of the individual compounds and the activity of the known synergistic active compound combinations is not always entirely satisfactory in all fields of application, in particular when low application rates are used.

It has now been found that the new active compound combinations of the 2-cyanobenzimidazoles of the formula

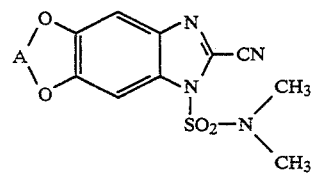

(I)

A=—CF$_2$—      (I-1)

A=—CF$_2$—CF$_2$—      (I-2)

at least
(A) one azole derivative of the formula,

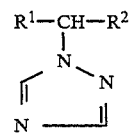

(II)

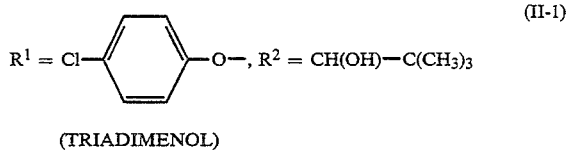

(II-1)

$R^1 = Cl$—⟨phenyl⟩—O—, $R^2 = CH(OH)$—$C(CH_3)_3$ (TRIADIMENOL)

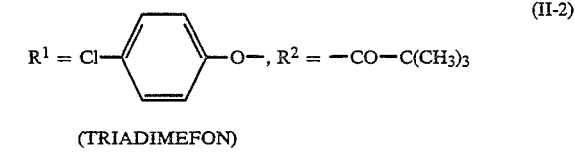

(II-2)

$R^1 = Cl$—⟨phenyl⟩—O—, $R^2 = $—CO—$C(CH_3)_3$ (TRIADIMEFON)

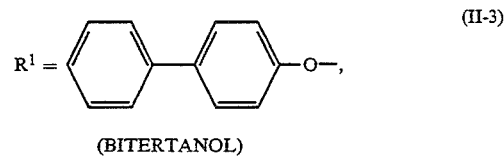

(II-3)

$R^1 = $ ⟨biphenyl⟩—O—, (BITERTANOL)

$R^2 = $ —CH(OH)—C(CH$_3$)$_3$ and/or
(B) one azole derivative of the formula

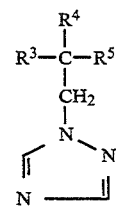

(III)

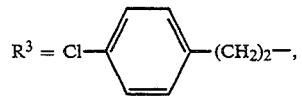

$R^3 = Cl$—⟨phenyl⟩—(CH$_2$)$_2$—, (TEBUCONAZOLE)

$R^4 = $ —C(CH$_3$)$_3$, $R^5 = $ OH,

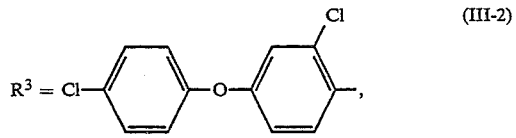

(III-2)

$R^3 = Cl$—⟨phenyl⟩—O—⟨phenyl⟩-Cl, $R^4$ and $R^5$ together represent —OCH$_2$CH(CH$_3$)O—

(DIFENCONAZOLE)

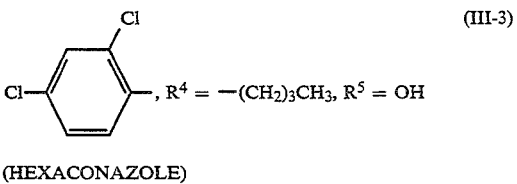

(III-3)

$R^3 = Cl$—⟨phenyl⟩-Cl, $R^4 = $ —(CH$_2$)$_3$CH$_3$, $R^5 = $ OH (HEXACONAZOLE)

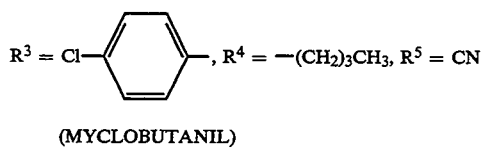
(MYCLOBUTANIL)

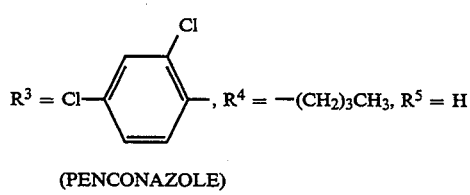
(PENCONAZOLE)

and/or
(C) the azole derivative

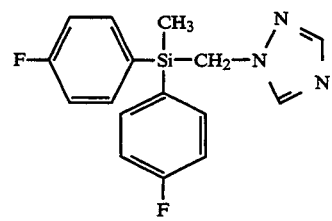
(FLUSILAZOLE)

and/or
(D) the azole derivative of the formula

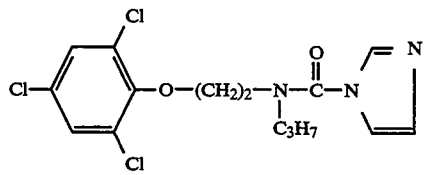
(PROCHLORAZ)

and/or
(E) the compound of the formula

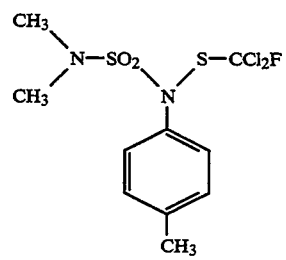
(TOLYLFLUANID)

and/or
(F) a compound of the formula

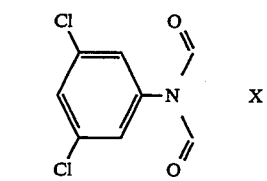

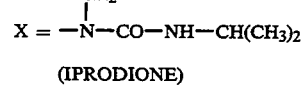
(IPRODIONE)

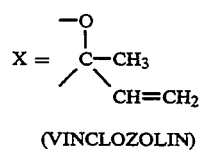
(VINCLOZOLIN)

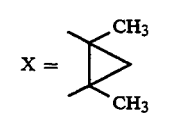
(PROCYMIDONE)

and/or
(G) the compound of the formula

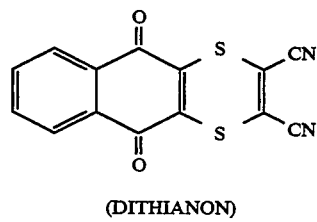
(DITHIANON)

and/or
(H) the compound of the formula

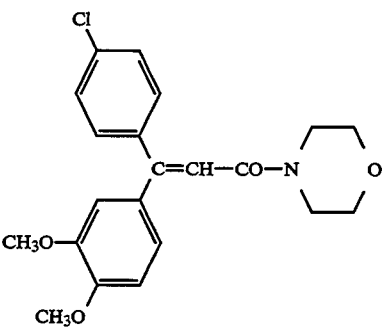
(DIMETHOMORPH)

and/or
(I) the compound of the formula and/or
(K) a compound of the formula (XI)

R⁶ = —C≡C—CH₃ (XI-1)
(MEPANIPYRIM)

R⁶ = CH₃ (XI-2)
(PYRIMETHANIL)

R⁶ = —◁ (XI-3)

(CYPRODINYL)

and/or
(L) the compound of the formula (XII)

and/or
(M) the compound of the formula (XIII)

and/or
(N) the compound of the formula (XIV)

have very good fungicidal properties.

Surprisingly, the fungicidal activity of the active compound combinations according to the invention is considerably higher than the total of the activities of the individual active compounds and also considerably higher than the activities of the known active compound combinations. Therefore, synergistic effect which could not have been predicted exists and not merely an additional effect.

The 2-cyanobenzimidazoles of the formula (I) and their use as fungicides have been disclosed (cf. EP-OS (European Published Specification) 0 517 476).

The fungicidal components also present in the active compound combinations according to the invention are also known. The individual active compounds are described in the following publications:

(A) Compounds of the formula (II)
DE-OS (German Published Specification) 2 201 063
DE-OS (German Published Specification) 2 324 010
DE-OS (German Published Specification) 2 737 489

(B) Compounds of the formula (III)
DE-OS (German Published Specification) 3 018 866
DE-OS (German Published Specification) 2 551 560
EP 47 594
DE 2 735 872

(C) Compound of the formula (IV)
EP 68 813
U.S. Pat. No. 4,496,551

(D) Compound of the formula (V)
DE-OS (German Published Specification) 2 429 523
DE-OS (German Published Specification) 2 856 974
U.S. Pat. No. 4,108,411

(E), (G) Compound of the formula (VI) and (VIII), respectively,
K. H. Büchel "Pflanzenschutz und Schädlingsbekämpfung" [Crop Protection and Pest Control]
Georg Thieme Verlag, Stuttgart 1977

(F) Compounds of the formula (VII),
DE 2 207 576
U.S. Pat. No. 3,903,090
U.S. Pat. No. 3,755,350
U.S. Pat. No. 3,823,240

(H) Compound of the formula (IX)
EP 219 756

(I) Compound of the formula (X)
EP 206 999

(K) Compound of the formula (XI)
EP 270 111
EP 310 550

(L) Compound of the formula (XII)
EP 382 375

(M) Compound of the formula (XIII)
EP 515 901

(N) Compound of the formula (XIV)
EP 472 996

Besides an active compound of the formula (I), the active compound combinations according to the invention contain at least one active compound from amongst the compounds of groups (A) to (N). In addition, they can also contain other, fungicidally active components which are admixed.

The synergistic effect is particularly pronounced when the active compound combinations according to the invention contain the active compounds in certain ratios by weight. However, the ratios by weight of the active compounds in the active compound combinations can be varied within a relatively wide range. In general,

- 0.1 to 50 parts by weight, preferably 1 to 20 parts by weight of active compound from amongst group (A),
- 0.1 to 50 parts by weight, preferably 1 to 20 parts by weight of active compound from amongst group (B),
- 0.1 to 50 parts by weight, preferably 1 to 20 parts by weight of active compound from amongst group (C),
- 0.1 to 50 parts by weight, preferably to 20 parts by weight of active compound from amongst group (D),
- 1 to 200 parts by weight, preferably 1 to 50 parts by weight of active compound from amongst group (E),
- 0.1 to 50 parts by weight, preferably 1 to 20 parts by weight of active compound from amongst group (F),
- 1 to 200 parts by weight, preferably 1 to 50 parts. by weight of active compound from amongst group (G),
- 0.1 to 50 parts by weight, preferably 1 to 20 parts by weight of active compound from amongst group (H),
- 0.1 to 50 parts by weight, preferably 1 to 20 parts by weight of active compound from amongst group (I),
- 0.1 to 50 parts by weight, preferably 1 to 20 parts by weight of active compound from amongst group (K),
- 0.1 to 50 parts by weight, preferably 1 to 20 parts by weight of active compound from amongst group (L),
- 0.1 to 50 parts by weight, preferably 1 to 20 parts by weight of active compound from amongst group (M), and
- 0.1 to 50 parts by weight, preferably 1 to 20 parts by weight of active compound from amongst group (N), are used per part by weight of active compound of the formula (I).

The active compound combinations according to the invention have very good fungicidal properties. They can be used, in particular, for combating phytopathogenic fungi, such as Plasmodiophoromycetes, Oomycetes, Chytridiomycetes, Zygomycetes, Ascomycetes, Basidiomycetes, Deuteromycetes and the like.

The active compound combinations according to the invention are particularly suitable for combating cereal diseases, such as Erysiphe, Cochliobolus, Pyrenophora and Leptosphaeria, and against fungal attack in vegetables, vines and fruit, for example against Venturia or Podosphaera in apples, Botrytis in beans and Phytophthora in tomatoes.

The good toleration, by plants, of the active compounds, at the concentrations required for combating plant diseases, permits treatment of aboveground parts of plants, of vegetative propagation stock and seeds, and of the soil.

The active compound combinations according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example, non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example ligninsulphite waste liquors and methylcellulose.

Adhesives such as carboxymethylcellulose and natural and synthetic polymers in the form of powders, granules or latices, such as arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanin dyestuffs and trace nutrients such as salts of iron, manganese, boron, copper, cobalt, molybdenum and zinc.

The formulations in general contain between 0.1 and 95 per cent by weight of active compound, preferably between 0.5 and 90%.

The active compound combinations according to the invention can be present in the formulations as mixtures with other known active compounds, such as fungicides, insecticides, acaricides and herbicides, and also as mixtures with fertilizers or plant growth regulators.

The active compound plant combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering and a powder for dry seed treatment, a solution for seed treatment, a water-soluble powder for seed treatment, a water-soluble powder for slurry treatment, or by encrusting. In the treatment of parts of plants, the concentrations of active compound in the use forms can be varied within a substantial range. In general, they are between 1 and 0.0001% by weight, preferably between 0.5 and 0.001%.

In the treatment of seed, amounts of 0,001 to 50 g of active compound per kilogram of seed are generally required, preferably 0.01 to 10 g.

In the treatment of the soil, active compound concentrations from 0.00001 to 0.1% by weight, preferably 0.0001 to 0.02% by weight, are required at the site of action.

The good fungicidal activity of the active compound combinations according to the invention can be seen from the examples which follow. While the individual active compounds or the known active compound combinations show weaknesses with regard to the fungicidal activity, the tables of the examples which follow show clearly that the activity found in the case of the active compound. combinations according to the invention exceeds the total of the activities of individual active compounds (synergism) and also exceeds the activities of the known active compound combinations.

A synergistic effect of fungicides is always present when the fungicidal activity of the active compound combinations exceeds the total of the activities of the active compounds when applied individually.

The activity to be expected for a given combination of two active compounds can be calculated as follows (cf. Colby, S. R., "Calculating Synergistic and Antagonistic Responses of Herbicide Combinations", Weeds 15, pages 20–22, 1967):

If

X denotes the degree of effectiveness expressed as a % of the untreated control when the active compound A is applied at a concentration of m ppm, Y denotes the degree of effectiveness expressed as a % of the untreated control when the active compound B is applied at a concentration of m ppm, E denotes the degree of effectiveness expressed as a % of the untreated control when the active compounds A and B are applied at concentrations of m and n ppm, $$\text{then } E = X + Y - \frac{X \cdot Y}{100}$$

If the actual fungicidal activity is greater than the calculated figure, then the combination is superadditive in its effectiveness i.e. a synergistic effect is present. In this case, the actually observed degree of effectiveness must exceed the value of the expected degree of effectiveness (E) calculated using the abovementioned formula.

EXAMPLE 1

Phytophthora Test (tomato)/protective

To produce a suitable preparation of active compound, commercially available formulations of active compounds (individual active compounds or active compound combinations) are diluted with water to the concentration desired in each case.

To test for protective activity, young plants are sprayed with the preparation of active compound until dripping wet. After the spray coating has dried on, the plants are inoculated with an aqueous spore suspension of Phytophthora infestans.

The plants remain in an incubation cabin at approximately 20° C. and 100% relative atmospheric humidity.

3 days after inoculation, the test is evaluated.

The table which follows shows the active compounds, concentrations of active compounds and test results.

TABLE 1

| Active Compounds | Phytophthora Test (Tomato)/protective | |
|---|---|---|
| | Concentration of active compounds in ppm | Degree of Effectiveness in % of the untreated control |
| known mixture | | |
| (I-1) + CH₃\N—SO₂—N—S—CCl₂F /CH₃ (phenyl) | 0.5 + 4 | 53 |
| Mixture according to the invention: | | |
| (I-1) + (VI) | 0.5 + 4 | 86 |
| Known mixtures | | |
| (I-2) + | | |

TABLE 1-continued

Phytophthora Test (Tomato)/protective

| Active Compounds | Concentration of active compounds in ppm | Degree of Effectiveness in % of the untreated control |
|---|---|---|
| CH₃–N(CH₃)–SO₂–N(C₆H₅)–S–CCl₂F | 0.5 + 4 | 78 |
| (I-2) + CH₃–N(CH₃)–SO₂–N(C₆H₅)–S–CCl₂F | 0.25 + 2 | 36 |

Mixtures according to the invention

| | | |
|---|---|---|
| (I-2) + (VI) | 0.5 + 4 | 86 |
| (I-2) + (VI) | 0.25 + 2 | 72 |
| (I-1) [structure with N(CH₃)₂, SO₂, NC, N, phenyl with OCF₂O] | 0.5 | 57 |
| (VII-3) [3,5-dichlorophenyl succinimide with CH₃ groups] | 4 | 0 |

Mixture according to the invention

| | | |
|---|---|---|
| (I-1) + (VII-3) | 0.5 + 4 | calc. 57* to 88** |
| (I-1) [structure with N(CH₃)₂, SO₂, NC, N, phenyl with OCF₂O] | 0.5 | 57 |

TABLE 1-continued

Phytophthora Test (Tomato)/protective

| Active Compounds | Concentration of active compounds in ppm | Degree of Effectiveness in % of the untreated control |
|---|---|---|
| (VII-1) [3,5-dichlorophenyl hydantoin with N—CO—NH—CH(CH₃)₂] | 4 | 0 |
| Mixture according to the invention | | |
| (I-1) + (VII-1) | 0.5 + 4 | calc. 57* fo. 65** |
| (I-1) | 0.5 | 57 |
| (VII-2) [3,5-dichlorophenyl with isopropenyl substituent] | 4 | 0 |
| Mixture according to the invention | | |
| (I-1) + (VII-2) | 0.5 + 4 | calc. 57* fo. 67** |
| (I-2) | 0.25 | 36 |
| (IX) | 0.25 | 12 |

TABLE 1-continued
Phytophthora Test (Tomato)/protective
| Active Compounds | Concentration of active compounds in ppm | Degree of Effectiveness in % of the untreated control |
|---|---|---|
| Mixture according to the invention | | |
| (I-2) + (IX) | 0.25 + 0.25 | calc. 44* <br> fo. 75** |
| 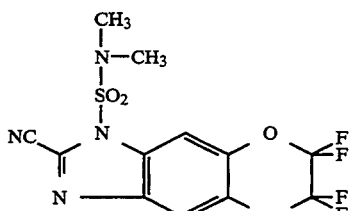 (I-2) | 0.25 | 36 |
| 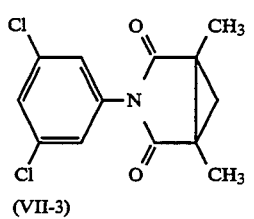 (VII-3) | 0.2 | 0 |
| Mixture according to the invention | | |
| (I-2) + (VII-3) | 0.25 + 2 | calc. 44* <br> fo. 90** |
| 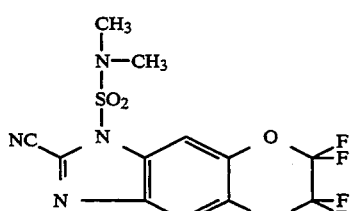 (I-2) | 0.25 | 36 |
| 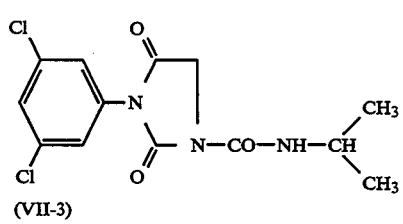 (VII-3) | 2 | 0 |
| Mixture according to the invention | | |
| (I-2) + (VII-3) | 0.25 + 2 | calc. 36* <br> fo. 92** |

TABLE 1-continued

Phytophthora Test (Tomato)/protective

| Active Compounds | Concentration of active compounds in ppm | Degree of Effectiveness in % of the untreated control |
|---|---|---|
| (I-2) [structure: NC-C(=N-)-N(SO$_2$-N(CH$_3$)CH$_3$)-aryl with -O-CF$_2$-CF$_2$-O- dioxine ring] | 0.25 | 36 |
| (VII-2) [structure: 3,5-dichlorophenyl-N(C(=O)OCH(CH$_3$)(CH=CH$_2$))-C(=O)-] | 2 | 0 |
| Mixture according to the invention | | |
| (I-2) + (VII-2) | 0.25 + 2 | calc. 36* fo. 90** |

*Expected value, calculated using Colby's formula (see above)
**found

EXAMPLE 2

Botrytis Test (beans)/protective

To produce a suitable preparation of active compound, commercially available formulations of active compounds (individual active compounds or active compound combinations) are diluted with water to the concentration desired in each case.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity at 20° C.

3 days after the inoculation, the size of the infected spots on the leaves is evaluated.

To demonstrate the synergism between the active compounds used in this test, the results were evaluated by the method described by Colby (see above).

The table which follows shows the active compounds, concentrations of active compounds and test results.

TABLE 2

Botrytis Test (beans)/protective

| Active Compounds | Concentration of active compounds in ppm | Degree of Effectiveness in % of the untreated control |
|---|---|---|
| (I-2) [structure as above] | 2 | 0 |

TABLE 2-continued
Botrytis Test (beans)/protective
| Active Compounds | Concentration of active compounds in ppm | Degree of Effectiveness in % of the untreated control |
|---|---|---|
| 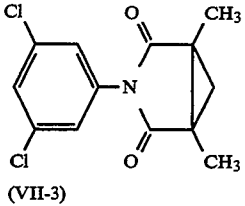 (VII-3) | 20 | 17 |
| Mixture according to the invention | | |
| (I-2) + (VII-3) | 2 + 20 } | calc. 17* fo. 44** |
| 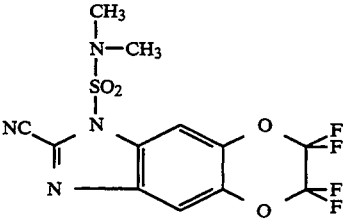 (I-2) | 2 | — 0 |
| 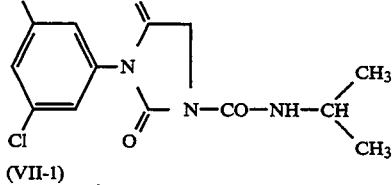 (VII-1) | 20 | 49 |
| Mixture according to the invention | | |
| (I-2) + (VII-1) | 2 + 20 } | calc. 49* fo. 64** |
| 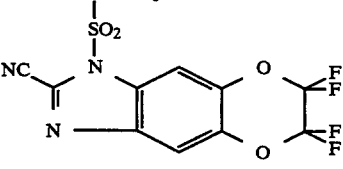 (I-2) | 2 | 0 |
| 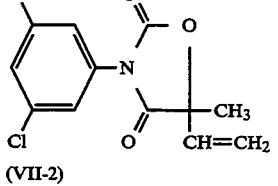 (VII-2) | 20 | 24 |
| Mixture according to the invention | | |
| (I-2) + | 2 + } | calc. 24* |

TABLE 2-continued

Botrytis Test (beans)/protective

| Active Compounds | Concentration of active compounds in ppm | Degree of Effectiveness in % of the untreated control |
|---|---|---|
| (VII-2) | 20 | fo. 41** |

*Expected value, calculated using Colby's formula (see above)
**found

It is understood that the specification and examples are illustrative but not limitative of the present invention and that other embodiments within the spirit and scope of the invention will suggest themselves to those skilled in the art.

What is claimed is:

1. A fungicidal composition comprising a synergistic fungicidally effective amounts of a combination of a compound of the formula

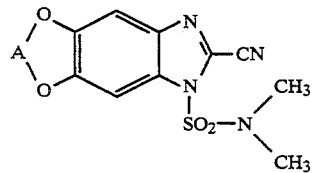

(I)

$A = -CF_2-$     (I-1)

$A = -CF_2-CF_2-$     (I-2)

and from about 1 to 20 times its weight of the compound of the formula

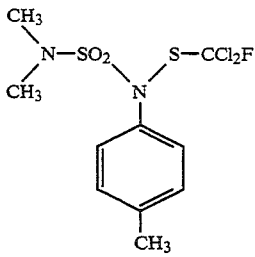

(VI)

2. A composition according to claim 1, wherein the compound (VI) is present in from about 1 to 8 times the weight of compound (I).

3. A method of combating fungi which comprises applying to such fungi or their habitat a synergistic fungicidally effective amount of a composition according to claim 1.

4. A method of combating Oomycetes which comprises applying to such Oomycetes or their habitat a synergistic fungicidally effective amount of a composition according to claim 2.

* * * * *